United States Patent [19]
Dolfini

[11] 4,000,134
[45] Dec. 28, 1976

[54] 7-METHOXY PYRIDYLUREIDOCEPHALOSPORINS
[75] Inventor: Joseph Edward Dolfini, Princeton, N.J.
[73] Assignee: E. R. Squibb & Sons, Inc., Princeton, N.J.
[22] Filed: Aug. 23, 1973
[21] Appl. No.: 390,814
[52] U.S. Cl. ............ 260/243 C; 260/294.9; 260/295 R; 260/295 L; 260/295.5 R; 260/296 R; 260/297 R; 424/246
[51] Int. Cl.² ............................ C07D 501/36
[58] Field of Search ....................... 260/243 C
[56] References Cited
UNITED STATES PATENTS

| 3,833,568 | 9/1974 | Dolfini et al. | 260/243 C |
| 3,843,641 | 10/1974 | Christensen et al. | 260/243 C |
| 3,860,591 | 1/1975 | Breuer | 260/243 C |

Primary Examiner—Nicholas S. Rizzo
Assistant Examiner—David E. Wheeler
Attorney, Agent, or Firm—Lawrence S. Levinson; Merle J. Smith; Stephen B. Davis

[57] ABSTRACT

Compounds of the formula

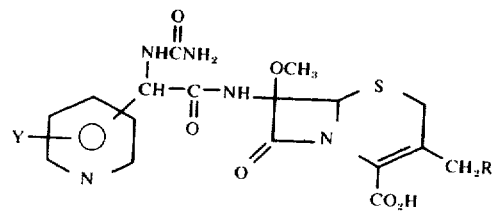

wherein R is H, heterocyclic thio, pyridinium, carbamoyloxy or acetoxy; Y is H, Cl or Br; and pharmaceutically acceptable salts and esters thereof are effective antibacterial agents.

3 Claims, No Drawings

7-METHOXY PYRIDYLUREIDOCEPHALOSPORINS

BACKGROUND OF THE INVENTION

Derivatives of 6-aminopenicillanic acid and of 7-aminocephalosporanic acid are known and have been described as antibacterial agents. There is, however, a continuing need for new antibacterial agents which are effective against additional gram-positive and gram-negative organisms, are effective against resistant organisms or which may be utilized when bacteria develop resistance to known antibacterial agents, or which are particularly effective against certain hard to control organisms.

SUMMARY OF THE INVENTION

This invention relates to new 7-methoxy pyridylureidocephalosporins of the general formula

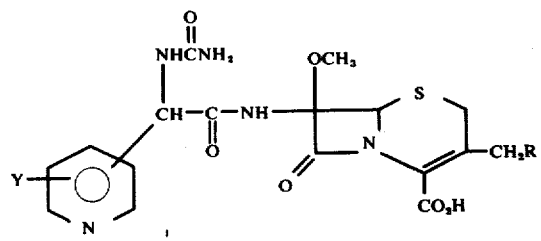

wherein R is H, heterocyclic thio, e.g. pyridyl-1-oxo-2-thio, 3-methyl-1,2,4-thiadiazolythio, 1-methyl-tetrazolyl-5-thio, 2-methyl-1,3,4-thiadiazolyl-5-thio; pyridinium, carbamoyloxy or acetoxy; Y is H, Cl or Br, and to pharmaceutically acceptable carboxylate salts, lower alkyl esters, haloloweralkyl esters or acyloxymethyl esters thereof. The compounds of the present invention are effective antibacterial agents and are useful in the treatment of many gram negative and gram positive infections. These compounds are useful as disinfectants and also as nutritional supplements in animal feeds. The 7-methoxy group occupies the α-configuration.

DETAILED DESCRIPTION

The compounds of the present invention may be prepared from a heterocyclic aldehyde of the formula

(I)

The heterocyclic aldehyde (I) is first converted to an amino acid by known methods, for example, by the well known Strecker amino acid synthesis, Ann 75, 27 (1850); 91, 349 (1854). This method involves the synthesis of α-amino acids by the simultaneous reaction of aldehydes with ammonia and hydrogen cyanide followed by hydrolysis of the resulting amino nitriles. As applied to the heterocyclic aldehyde I of the present invention the reaction is as follows:

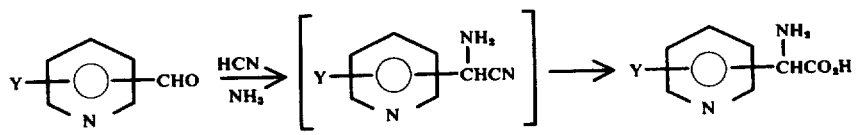

In addition, various well known modifications of the Strecker synthesis may be employed. For example, the Erlenmeyer modification:

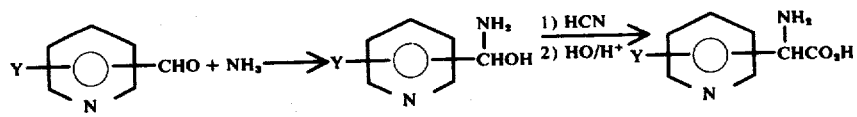

the Tiemann modification:

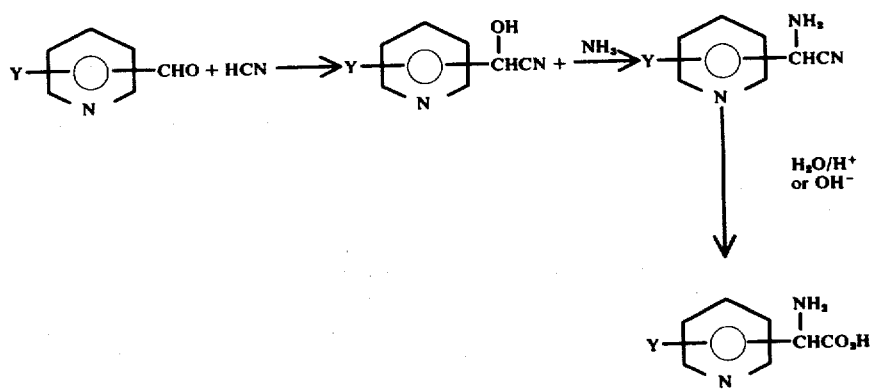

The Zelinsky-Stadnikoff modification:

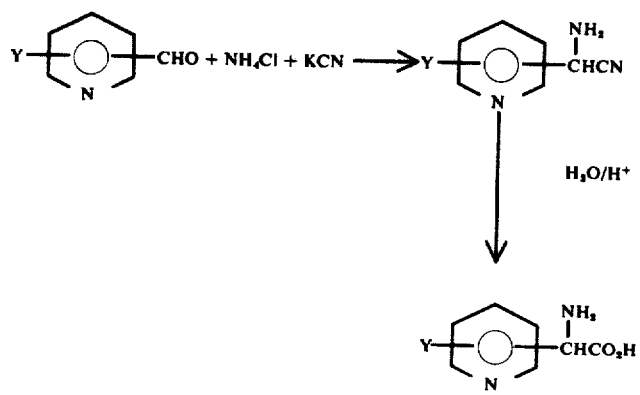

or the Bucherer modification:

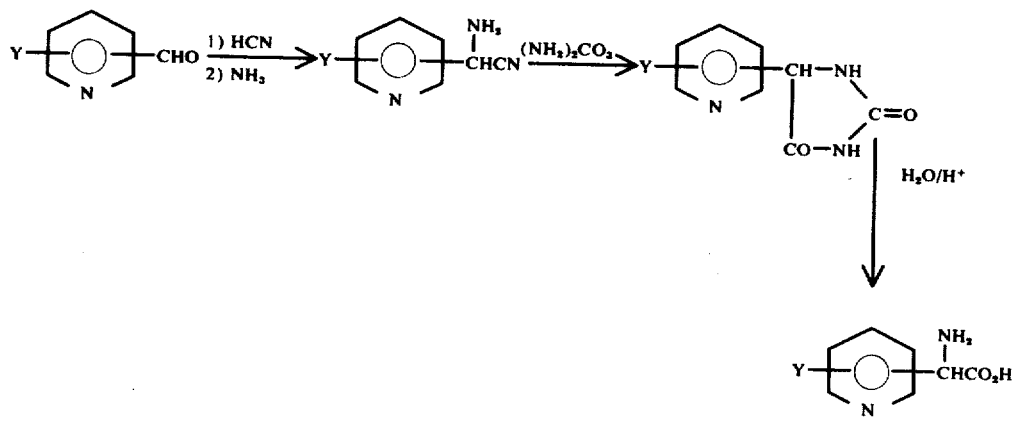

The amino acid of the formula

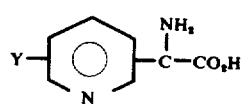 (II)

produced by any suitable method, for example, those described above, is then reacted with an alkali metal cyanate or an alkaline earth metal cyanate to form an α-ureido compound of the formula

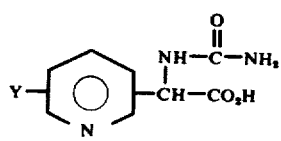 (III)

This reaction takes place by treating an aqueous suspension of the α-amino acid with the alkali or alkaline earth metal cyanate. Acidification with hydrochloric acid precipitates the α-ureido acid in good yield. A solution of the α-ureido acid in an organic solvent containing a tri-(lower)alkyl amine is converted to a mixed carbonic or other anhydride (IV) by treating with an anhydride forming reagent, e.g., a lower alkyl chloroformate, an aryl chloroformate, or an acyl halide, at reduced temperatures of from about 0° C to about −20° C. The reaction takes place in a solvent such as methylene chloride, chloroform, dioxane, dimethoxyethane, benzene, aqueous acetone or dimethoxyethane, acetonitrile, or dimethylformamide.

Reaction at reduced temperatures of the mixed anhydride (IV) with a protected ester, e.g., benzhydryl, trichloroethyl, or tertiarybutyl of a compound of the formula

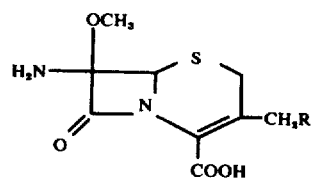 (VII)

wherein R is as previously defined yields the compounds of the present invention as the corresponding protected ester wherein R is acetoxy, H or carbamoyloxy, respectively, after removal of the ester group.

Compounds of formula V wherein R is heterocyclic thio may be obtained from an acylated 7-AMCA by methods known in the art for the formation of 7-aminocephalosporanic acid analogs, e.g., Abraham and Newton (1950) Ciba Foundation Symposium, Amino Acids, Peptides, Antimetabolic Activity, p. 205; U.S. Pat. No. 3,225,038; and Belgian patents 641,338 and 652,148.

Alternatively, a compound of formula V may be obtained by converting a compound of formula III to an activated ester or by reacting a compound of formula III with a carboxyl group activating agent, such as, for example, dicyclohexylcarbodiimide or bisimidazole carbonyl, and then coupling the activated form of the compound of formula III with a protected ester of 7-AMCA or a protected ester of 7-AMDCA. In some cases, as will be obvious to those skilled in the art, the carboxyl group may be activated by conversion to an acid halide, e.g., the chloride, or to an azide prior to coupling with a protected ester of 7-AMCA or a protected ester of 7-AMDCA. A more detailed discussion of carboxyl activating groups may be obtained by reference to standard works on peptide synthesis, for example, Bodanszky et al., "Peptide Synthesis", Interscience, 1966.

Alternatively, the α-amino acid (II) produced, for example, by subjecting the heterocyclic aldehyde to the Strecker reaction or a modification thereof, may be used to acylate a protected ester of 7-AMCA or a protected ester of 7-AMDCA. The resulting α-amino acid derivative of 7-AMCA or 7-AMDCA is then reacted with an alkali metal cyanate or an alkaline earth metal cyanate in the presence of water to form the compounds (V) of the present invention.

The α-amino acid (II) or the α-ureido acid (III) obtained occurs as a racemate of D and L optical isomers. It is generally possible to resolve these compounds by using optically pure bases (or acids) using methods known to the art, for example, as described by L. Velluz, "Substances Naturelle de Synthesese," 9, pp. 119-174 (1954), or E. L. Eliel, "Stereochemistry of Carbon Compounds," Chapter 4, McGraw-Hill Book Co., N.Y. (1962). The resulting pure D or L acid may then be coupled to a protected ester of the 7-AMCA or a protected ester of the 7-AMDCA moiety. Generally the coupling of the D form leads to the more active product.

When preparing compounds of the present invention according to the reaction sequence wherein a protected ester of 7-AMCA or of 7-AMDCA is acylated with an α-amino acid of formula II, it may be desirable to protect the α-amino group during the acylation reaction by means of an amino protecting group. Such amino protecting groups are well known in the art and are described, for example, by Bodanszky et al., "Peptide Synthesis," supra.

Specific examples of methods for acylating 7-AMCA or 7-AMDCA are similar to those described for the acylation of 7-ACA or 7-ADCA, for example, in Netherlands Pat. No. 6,812,382, Belgian Patent 675,298, as well as in the following articles:

Spencer et al., J. Med. Chem., 9, 746 (1966);
Ryan et al., ibid, 12, 310 (1969).

A general reaction scheme for preparing compounds of the present invention is shown below wherein for ease of representation Z is the residue of 7-AMCA or 7-AMDCA:

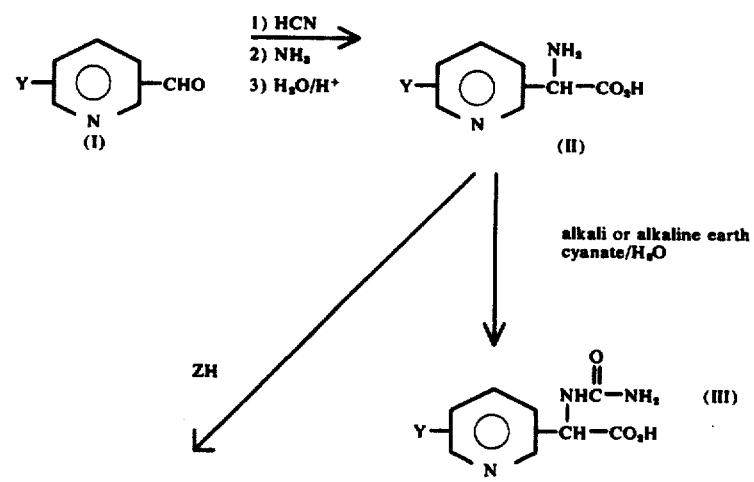

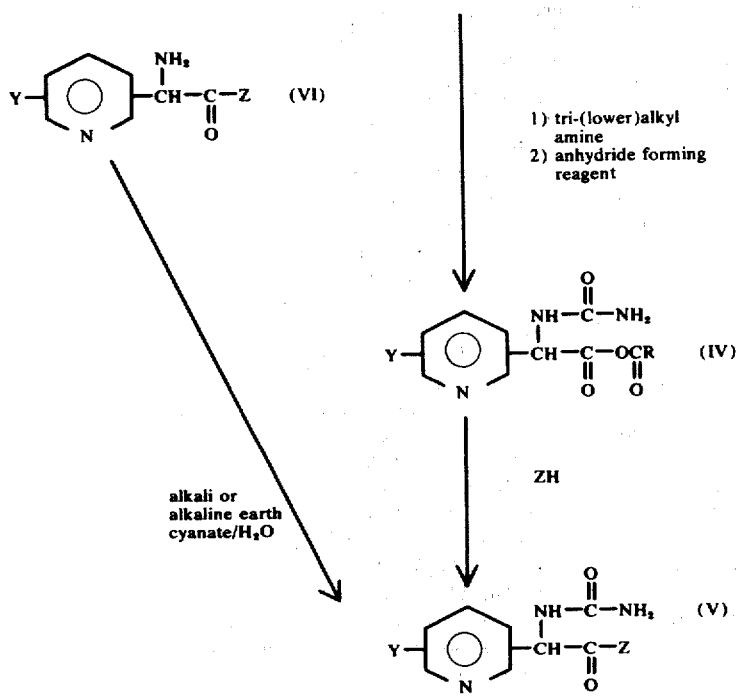

The carboxylate salts of the compounds (V) of the present invention are formed by reacting the carboxyl group of the 7-AMCA or 7-AMDCA moiety with a salt-forming ion, e.g., an alkali metal such as sodium or potassium, or an alkaline earth metal such as magnesium or calcium, or a metal of group IIIA such as aluminum, or the radical of an organic base such as dibenzylamine, N,N-dibenzylethylenediamine or other organic bases known to form salts with cephalosporanic acids.

The lower alkyl esters may be obtained by esterifying the carboxyl group of the 7-AMCA or 7-AMDCA moiety with a straight or branched chain lower alkyl halide of from 1 to 3 carbon atoms, e.g., methyl chloride, ethyl bromide and the like, or with a diazoalkane of from 1 to 3 carbon atoms, e.g., diazomethane, diazoethane, and the like. The resulting ester group is then formed by a radical such as methyl, ethyl, propyl, or isopropyl.

The acyloxymethyl esters may be obtained according to known methods, for example a method adapted from that of Daehne et al., J. Med. Chem. 13, 607 (1970), by reacting the carboxyl group or a metal salt thereof of the 7-AMCA or 7-AMDCA moiety with a halide of the formula

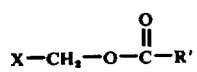

wherein R' may be lower alkyl of up to 5 carbon atoms, phenyl, benzyl or phenethyl, and X is chlorine or bromine. Thus, suitable compounds include acetoxymethyl chloride, propionyloxymethyl chloride, butyryloxymethyl chloride, pivaloyloxymethyl chloride, valeryloxymethyl chloride, benzoyloxymethyl chloride, or phenacetoxymethyl chloride, and the like.

It will be appreciated that certain of the compounds of this invention exist in various states of solvation as well as in different optically active forms. The various forms as well as their mixtures are within the scope of this invention.

The compounds of this invention have a broad spectrum of antibacterial activity against both gram positive and gram negative organisms such as *Staphylococcus aureus, Salmonella schottmuelleri, Proteus vulgaris, Escherichia coli* and *Streptococcus pyogenes*. They may be used as antibacterial agents in a prophylactic manner, e.g., in cleaning or disinfecting compositions, or otherwise to combat infections due to organisms such as those named above, and in general may be utilized in a manner similar to cephalosporin C, cephalothin and other cephalosporins. For example, a compound of formula V or a physiologically acceptable salt or ester thereof may be used in various animal species in an amount of about 1 to 200 mg./kg. daily, orally or parenterally, in single or two to four divided doses to treat infections of bacterial origin.

Up to about 600 mg. of a compound of formula V or a pharmaceutically acceptable salt or ester thereof may be incorporated in an oral dosage form such as tablets, capsules or elixirs or in an injectable form in a sterile aqueous vehicle prepared according to conventional pharmaceutical practice.

In cleaning or disinfecting compositions, e.g., in barns or dairy equipment, a concentration of about 0.01 to 1% by weight of such compounds admixed with, suspended or dissolved in conventional inert dry or aqueous carriers for application by washing or spraying may be used.

They are also useful as nutritional supplements in animal feeds.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

In the compound of formula VII wherein R is as previously defined

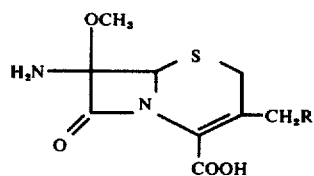

the 7-methoxy group has the α-configuration

The following examples illustrate the present invention without, however, limiting the same thereto.

EXAMPLE 1

7-[2-Ureido-2-(2-pyridyl)acetamido]-7-methoxycephalosporanic acid

2-Pyridylcarboxaldehyde is reacted with ammonium cyanide prepared in situ from ammonium chloride and sodium cyanide. The resulting amino nitrile is hydroyzed to yield pyridyl-2-(2-amino)acetic acid. A suspension of the latter compound (0.10 moles) in 150 ml. of water is treated with 8.1 g. of potassium cyanate. The resulting mixture is heated to about 80° C to give a clear solution which is then allowed to stand at room temperature for about 24 hours. Acidification to pH 3.5–5 with hydrochloric acid precipitates the α-ureido compound. A solution containing 0.10 moles of the α-ureido acid in 100 ml. of acetone containing 10.1 g of triethylamine at a temperature of from about 0° C to about −20° C is converted to a mixed carbonic anhydride by treating with 10.8 g. of ethyl chloroformate for about 30 minutes. A cold (about −10° C) solution of 30.3 of 7-amino-7-methoxycephalosporanic acid, benzyhydryl ester in 400 ml. of 1:1 acetone-water containing 10.1 g of triethylamine is added to the solution of mixed anhydride and the reaction mixture stirred vigorously at about 0° C for approximately 30–45 minutes. The volume of the solution is reduced by evaporating the bulk of the acetone at reduced pressure at room temperature or below. One liter of ethyl acetate is added and the solution washed with 2 × 200 ml of ice cold 5% aqueous sodium bicarbonate, 100 ml of water, 2 × 200 ml of 0.5 molar hydrochloric acid, and 100 ml again of water. The ethyl acetate solution is dried ($Na_2SO_4$) and evaporated to deposit the benzhydryl ester of the title compound.

The free acid is obtained by dissolving the ester (1 g) and anisole (500 mg) in 20 ml of ice cold trifluoroacetic acid and keeping it at 0–5° C for 30 minutes. The acid solvent is evaporated at reduced pressure. The residue is treated with 50 ml of water and the pH adjusted to 7.5 to dissolve the product. The solution is washed with ethyl acetate. (Lyophilization of the aqueous solution deposits the sodium salt of the title compound). The aqueous layer is acidified to precipitate the title compound.

EXAMPLE 2

7-[2-Ureido-2-(2-pyridyl)acetamido[-7-methoxy-3-desacetoxy cephalosporanic acid

Following the procedure of example 1 but substituting 24.5 g of 7-amino-7-methoxy-3-desacetoxycephalosporanic acid for 7-amino-7-methoxycephalosporanic acid, the title compound is obtained.

EXAMPLE 3

Pivaloyloxymethyl ester of 7-[2-ureido-2-(2-pyridyl)-acetamido]-7-methoxy-3-desacetoxy cephalosporanic acid Chloromethylpivalate (20 mmole) is combined with 10 mmole of the product of example 2, 0.4 ml. of a 5% aqueous sodium iodide solution, and 170 ml. of acetone. Triethylamine, 2.0 gm. (20 mmole), is added and the mixture stirred for 10 hours, then refluxed for one hour. The reaction mixture is cooled and concentrated in vacuo. The residue is partitioned between ethyl acetate, and 5% aqueous sodium bicarbonate. The organic layer is dried over sodium sulfate and evaporated to give the crude product which is obtained as a powder upon trituration with ether.

EXAMPLE 4

Pivaloyloxymethyl ester of 7-[2-ureido-2-(2-pyridyl)acetamido]-7-methoxy cephalosporanic acid Following the procedure of example 3 but substituting 10 mmole of the product of example 1 for the product of example 2, the title compound is obtained.

EXAMPLE 5

7-[2-Ureido-2-(2-pyridyl)acetamido]-7-methoxy-3-desacetoxy cephalosporanic acid, methyl ester A 0.1 molar solution of the product of example 2 in dimethoxyethane is treated with an excess of ethereal diazomethane. Evaporation of the solvent at reduced pressure deposits the title compound.

EXAMPLE 6

Acetoxymethyl ester of 7-[2-Ureido-2-(2-pyridyl)acetamido]-7-methoxycephalosporanic acid Following the procedure of example 4 but substituting chloromethylacetate for chloromethylpivalate, the title compound is obtained.

EXAMPLES 15 – 20

Following the procedure of example 2 but substituting for 2-pyridylcarboxaldehyde an equivalent amount of the aldehyde indicated in column I, there is obtained the 7-methoxydesacetoxycephalosporanic acid indicated in column II.

|     | I | II |
| --- | --- | --- |
| 15. | 3-pyridylcarboxaldehyde | 7-[2-Ureido-2-(3-pyridyl)acetamido]-7-methoxy-3-desacetoxy-cephalosporanic acid |
| 16. | 4-pyridylcarboxaldehyde | 7-[2-Ureido-2-(4-pyridyl)acetamido]-7-methoxy-3-desacetoxy-cephalosporanic acid |
| 17. | 4-chloro-2-pyridyl-carboxaldehyde | 7-[2-Ureido-2-(4-chloro-2-pyridyl)-acetamido]-7-methoxy-3-desacetoxy-cephalosporanic acid |
| 18. | 4-chloro-3-pyridyl-carboxaldehyde | 7-[2-Ureido-2-(4-chloro-3-pyridyl)-acetamido]-7-methoxy-3-desacetoxy-cephalosporanic acid |
| 19. | 5-chloro-3-pyridyl-carboxaldehyde | 7-[2-Ureido-2-(5-chloro-3-pyridyl)-acetamido]-7-methoxy-3-desacetoxy-cephalosporanic acid |
| 20. | 5-bromo-3-pyridyl-carboxaldehyde | 7-[2-Ureido-2-(5-bromo-3-pyridyl)-acetamido]-7-methoxy-3-desacetoxy-cephalosporanic acid |

EXAMPLE 7

7-[2-Ureido-2-(2-pyridyl)acetamido]-7-methoxycephalosporanic acid, potassium salt One millimole of the product of example 1 is dissolved in 10 ml. of a 0.01 N aqueous KOH solution. Lyophilization of the solution yields the title compound.

EXAMPLE 8

7-[2-Ureido-2-(2-pyridyl)acetamido]-7-methoxy-3-desacetoxycephalosporanic acid, calcium salt One millimole of the product of example 2 is dissolved in 10 ml. of a 0.05 N aqueous Ca(OH)$_2$ solution. Lyophilization of the solution yields the title compound.

EXAMPLES 9 – 14

Following the procedure of example 1 but substituting for 2-pyridylcarboxaldehyde an equivalent amount of the aldehyde indicated in column I, there is obtained the 7-methoxycephalosporanic acid indicated in column II.

EXAMPLE 21

7-[2-Ureido-2-(2-pyridyl)acetamido]-7-methoxycephalosporanic acid, N,N'-dibenzylethylenediamine salt A solution of 0.010 mol. of the product of example 1 in 25 ml of ethanol is added to a solution of 1.20 g. of N,N'-dibenzylthylenediamine in 25 ml. of ethanol at room temperature. After 15 minutes stirring the solvent is evaporated to deposit the title compound.

EXAMPLE 22

7-[2-Ureido-2-(2-pyridyl)acetamido]-7-methoxy-3-[2-(5-methyl-1,3,4-thiadiazolyl)-thiomethyl]-Δ$^3$-cephem-4-carboxylic acid A solution (0.026 mole) of the product of example 1, NaHCO$_3$ (2.1 g) and 3.8 g 2-mercapto-5-methyl-1,3,4-thiadiozole in 200 ml of pH 6.4 phosphate buffer is stirred for 5.5 hours at 60° C. The reaction is cooled to room temperature, acidified to pH 3 and extracted with ethyl acetate. The ethyl acetate layer is worked with saturated NaCl solution, dried (Na$_2$SO$_4$), and evaporated at reduced pressure to deposit the product.

EXAMPLE 23

7-[2-Ureido-2-(2-pyridyl)acetamido]-7-methoxy-3-carbamoyloxy-methyl-Δ$^3$-cephem-4-carboxylic acid

|     | I | II |
| --- | --- | --- |
| 9.  | 4-chloro-2-pyridyl-carboxaldehyde | 7-[2-Ureido-2-(4-chloro-2-pyridyl)-acetamido]-7-methoxycephalosporanic acid |
| 10. | 3-pyridylcarboxaldehyde | 7-[2-Ureido-2-(3-pyridyl)acetamido]-7-methoxy-cephalosporanic acid |
| 11. | 4-chloro-3-pyridyl-carboxaldehyde | 7-[2-Ureido-2-(4-chloro-3-pyridyl)-acetamido]-7-methoxycephalosporanic acid |
| 12. | 5-chloro-3-pyridyl-carboxaldehyde | 7-[2-Ureido-2-(5-chloro-3-pyridyl)-acetamido]-7-methoxycephalosporanic acid |
| 13. | 5-bromo-3-pyridyl-carboxaldehyde | 7-[2-Ureido-2-(5-bromo-3-pyridyl)-acetamido]-7-methoxycephalosporanic acid |
| 14. | 4-pyridylcarboxaldehyde | 7-[2-Ureido-2-(4-pyridyl)acetamido]-7-methoxycephalosporanic acid |

2-Pyridylcarboxaldehyde is reacted with ammonium cyanide prepared in situ from ammonium chloride and sodium cyanide. The resulting amino nitrile is hydrolyzed to yield thienyl-2-(2-amino)acetic acid. A suspension of the latter compound (0.10 moles) in 150 ml of water is treated with 8.1 g of potassium cyanate. The resulting mixture is heated to about 80° C to give a clear solution which is then allowed to stand at room temperature for about 24 hours. Acidification to pH 3.5 with hydrochloric acid precipitates the α-ureido compound. A solution containing 0.10 moles of the α-ureido acid in 100 ml of acetone containing 10.1 g of triethylamine at a temperature of from about 0° C to about −20° C is converted to a mixed carbonic anhydride by treating with 10.8 g of ethyl chloroformate for about 30 minutes. A cold (about −10° C) solution of 0.10 mol of 7-amino-7-methoxy-3-carbamoyloxymethyl-$\Delta^3$-cephem-4-carboxylic acid, benzhydryl ester in 400 ml of 1:1 acetone containing 10.1 g of triethylamine is added to the solution of mixed anhydride and the reaction mixture stirred vigorously at about 0° C for approximately 30–45 minutes. The volume of the solution is reduced by evaporating the bulk of the acetone at reduced pressure at room temperature or below.

One liter of ethyl acetate is added and the solution washed with 2 × 200 ml of ice cold 5% aqueous sodium bicarbonate, 100 ml of water, 2 × 200 ml of 0.5 molar hydrochloric acid, and 100 ml again of water. The ethyl acetate solution is dried ($Na_2SO_4$) and evaporated to deposit the benzhydryl ester of the title compound.

The free acid is obtained by dissolving the ester (1 g) and anisole (500 mg) in 20 ml of ice cold trifluoroacetic acid and keeping it at 0°–5° C for 30 minutes. The acid solvent is evaporated at reduced pressure. The residue is treated with 50 ml of water and the pH adjusted to 7.5 to dissolve the product. The solution is washed with ethyl acetate. (Lyophilization of the aqueous solution deposits the sodium salt of the title compound). The aqueous layer is acidified to precipitate the title compound.

EXAMPLE 24 – 26

Following the procedures of example 22 but substituting for 2-mercapto-5-methyl-1,3,4-thiadiozole, the heterocyclicthio compound listed below in column I, there is obtained respectively the final compound of column II.

|     | I | II |
| --- | --- | --- |
| 24. | Pyridinyl-1-oxo-2-thiol | 7-[2-Ureido-2-(2-pyridyl)-acetamido]-7-methoxy-3-[2-(1-oxo-pyridinyl)thiomethyl]-$\Delta^3$-cephem-4-carboxylic acid |
| 25. | 3-methyl-1,2,4-thiadiazolyl-5-thiol | 7-[2-Ureido-2-(2-pyridyl)acetamido]-7-methoxy-3-[5-(3-methyl-1,2,4-thiadiazolyl)thiomethyl]-$\Delta^3$-cephem-4-carboxylic acid |
| 26. | 1-methyltetrazolyl-5-thiol | 7-[2-Ureido-2-(2-pyridyl)acetamido]-7-methoxy-3-[5-(1-methyl-tetrazolyl)-thiomethyl]-$\Delta^3$-cephem-4-carboxylic acid |

EXAMPLE 27

7-[2-Ureido-2-(2-pyridyl)acetamido]-7-methoxy-3-[1-pyridiniummethyl]-$\Delta^3$-cephem-4-carboxylic acid A solution of 0.046 mole of the product of example 1, sodium salt, 10 g of potassium thiocyanate and 10 ml of pyridine in 50 ml of water is adjusted to pH 6.5 with 85% phosphoric acid and warmed to 60° for 6 hours. The solution is cooled to room temperature and extracted with a 25% solution of Amberlite LA-1 (acetate form) in methyl isobutylketone (6 × 100 ml). After standing overnight at 0 to 5° C the title compound separates.

EXAMPLE 28

A sterile powder for reconstitution for use intramuscularly is prepared from the following ingredients which supply 1000 vials each containing 250 mg. of active ingredient:

| | |
| --- | --- |
| 7-[2-Ureido-2-(2-pyridyl)acetamido]-7-methoxy cephalosporanic acid, Na salt, sterile | 250 mg. |
| Lecithin powder, sterile | 50 gm. |
| Sodium carboxymethylcellulose, sterile | 20 gm. |

The sterile powders are aseptically blended, subdivided, filled into sterile vials and sealed. The addition of 1 ml. of water for injection to the vial provides a suspension for intramuscular injection.

EXAMPLE 29

The following ingredients are admixed:

| | |
| --- | --- |
| 7-[Ureido-2-(2-pyridyl)acetamido]-7-methoxy-3-desacetoxy cephalosporanic acid | 250 gm. |
| Lactose | 56.9 gm. |
| Magnesium stearate | 3.1 gm. |

The mixed ingredients are subdivided and filled into 1000 No. 2 gelatin capsules each containing a total of 310 mg. with 250 mg. of active substance.

EXAMPLE 30

Tablets are prepared from the following ingredients:

| | |
| --- | --- |
| 7-[2-Ureido-2-(2-pyridyl)acetamido]-7-methoxy cephalosporanic acid, pivaloyloxymethyl ester | 5 kg. |
| Polyvinyl pyrrolidone | 360 gm. |
| Lactose | 780 gm. |
| Talc | 80 gm. |
| Magnesium stearate | 80 gm. |

The active substance is mixed with the lactose and granulated with an ethanol solution of the polyvinyl pyrrolidone. The wet material is screened and admixed with the talc and magnesium stearate. The mixture is compressed in a tableting machine to obtain 10,000 tablets weighing a total of 630 mg. each and containing 500 mg. of active ingredient.

What is claimed is:

1. The compound of the formula:

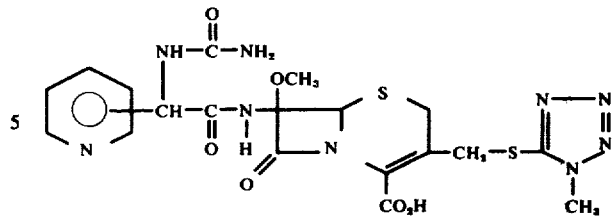

wherein the 7-methoxy group occupies the α-configuration; and pharmaceutically acceptable salts thereof.

2. The compound of the formula:

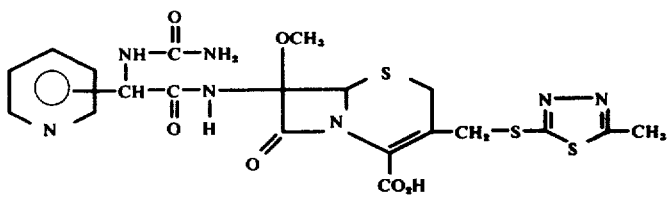

wherein the 7-methoxy group occupies the α-configuration; and pharmaceutically acceptable salts thereof.

3. The compound of the formula:

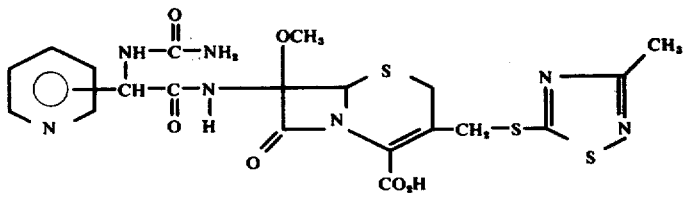

wherein the 7-methoxy group occupies the αconfiguration and pharmaceutically acceptable salts thereof.

* * * * *

UNITED STATES PATENT AND TRADEMARK OFFICE
CERTIFICATE OF CORRECTION

PATENT NO. : 4,000,134
DATED : December 28, 1976
INVENTOR(S) : Dolfini

It is certified that error appears in the above-identified patent and that said Letters Patent are hereby corrected as shown below:

Col. 2, line 3, after "esters," insert -- t-butyl ester, benzhydryl ester, --.

Col. 12, line 38 "thiadiazolyl)-" should read -- thiadiazolyl) --.

Col. 13, line 60, "tetrazolyl)-" should read -- tetrazolyl) --.

Col. 16, line 38, after "α" insert a hyphen (-).

Signed and Sealed this

Third Day of May 1977

[SEAL]

Attest:

RUTH C. MASON
*Attesting Officer*

C. MARSHALL DANN
*Commissioner of Patents and Trademarks*